United States Patent [19]

Huibers

[11] 4,371,616
[45] Feb. 1, 1983

[54] PROCESS FOR PRODUCING L-SUGARS

[75] Inventor: Derk T. A. Huibers, Pennington, N.J.

[73] Assignee: Hydrocarbon Research, Inc., Lawrenceville, N.J.

[21] Appl. No.: 296,094

[22] Filed: Aug. 26, 1981

[51] Int. Cl.³ .................... C12P 19/02; C07H 1/00; C07H 1/06

[52] U.S. Cl. ................................. 435/105; 536/1.1

[58] Field of Search ............... 435/105, 158; 426/658; 536/1

[56] References Cited

U.S. PATENT DOCUMENTS

| 2,207,768 | 7/1940 | Weijlard et al. | 435/823 |
| 4,036,694 | 7/1977 | Meguro et al. | 435/105 |
| 4,262,032 | 4/1981 | Levin | 426/658 |
| 4,322,569 | 3/1982 | Chao et al. | 568/863 |

Primary Examiner—Lionel M. Shapiro
Attorney, Agent, or Firm—Vincent A. Mallare; Wilson, Fred A.

[57] ABSTRACT

A method for producing L-sugars including L-idose and L-gulose from D-glucose. The method comprises hydrogenating D-glucose to provide sorbitol, oxydizing the D-sorbitol to provide L-sorbose, racemizing the L-sorbose to provide a mixture of L-sorbose, L-idose and L-gulose, and precipitating the L-sorbose with lime from a dilute solution. The unconverted L-sorbose is recovered by carbonation and recycled. The hydrogenation of glucose is done in a fixed catalyst bed.

23 Claims, 1 Drawing Figure

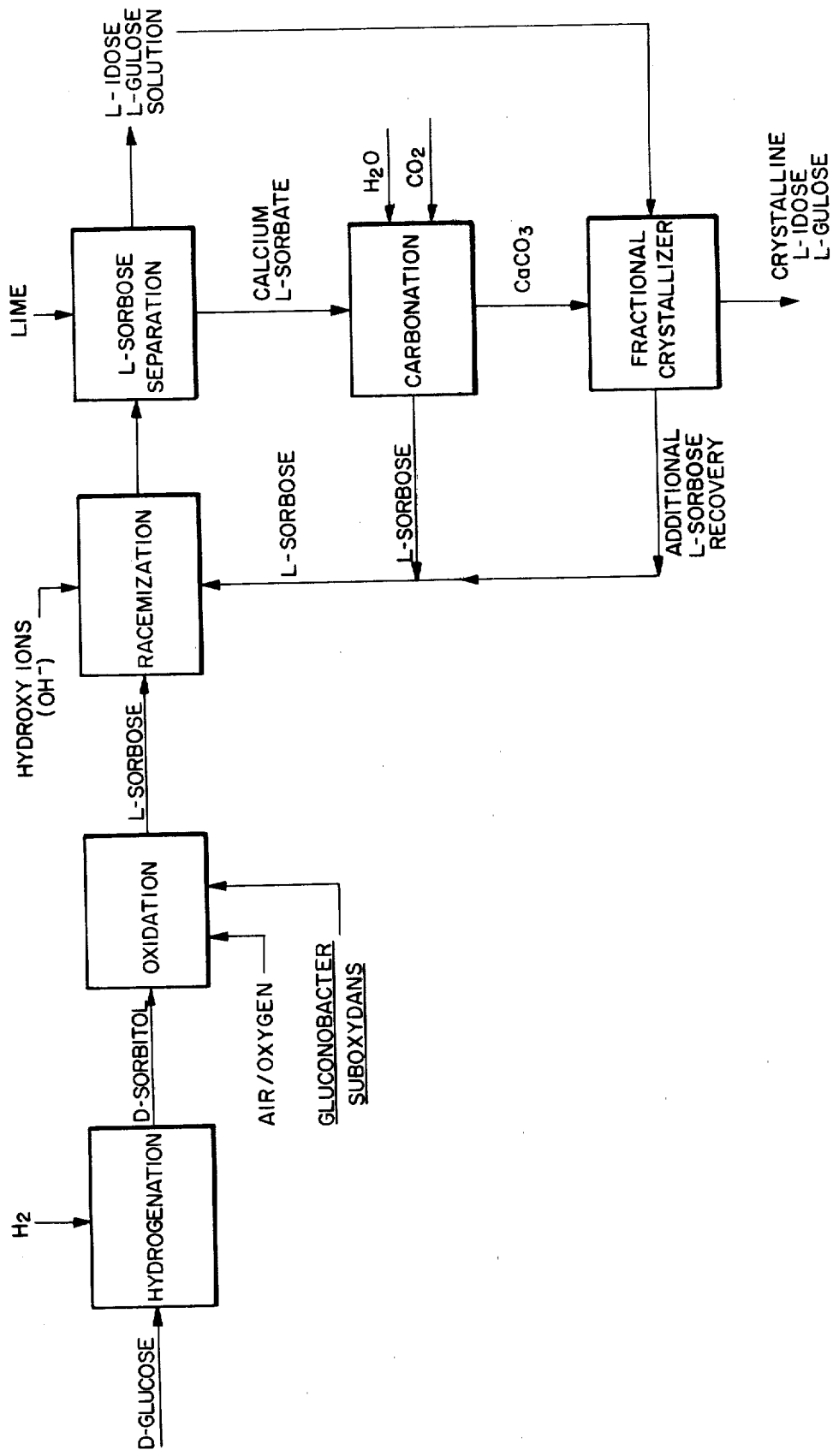

PROCESS FOR PRODUCING L-SUGARS

BACKGROUND OF INVENTION

This invention relates to L-sugars and more particularly to a method for commercially producing L-sugars for use as a sweetener for foodstuffs.

It has been known that sugars, i.e., D-sugars, such as D-glucose, D-fructose, D-saccharose, and others, have been useful as sweeteners. According to U.S. Pat. No. 4,262,032, it is now known that the use of L-sugars, such as L-gulose may be used as sweeteners for foodstuffs and are non-calorific.

The synthesis of L-sugars has generally been done experimentally in the laboratory and not on a commercial basis. However, since there is a need for producing sugars which are non-calorific, it would be advantageous to provide a method which could provide L-sugars such as those provided by the present invention economically and efficiently.

SUMMARY OF THE INVENTION

The present invention provides a method for producing L-sugars, including L-idose and L-gulose from D-glucose. The method comprises the steps of hydrogenating D-glucose to provide D-sorbitol, oxidizing the D-sorbitol to provide L-sorbose, racemizing the L-sorbose to a mixture of L-sorbose, L-idose and L-gulose, and precipitating the remaining L-sorbose with lime under cooling from a dilute solution. L-idose and L-gulose are recovered from the filtrate by crystallization. L-sorbose is recovered from the filtered solids by carbonation of the aqueous suspension and recycled.

BRIEF DESCRIPTION OF THE DRAWING

The present invention will be understood more clearly when considering the following detailed description in conjunction with the drawing; wherein:

FIG. 1 is a flow diagram of a process for preparing L-sugars according to the present invention.

DETAILED DESCRIPTION OF THE PREFERRED EMBODIMENT

Referring to FIG. 1, there is illustrated by means of a flow diagram, a process for preparing L-sugars according to the present invention. The L-sugars such as L-idose and L-gulose are the mirror image of corresponding D-sugars, i.e., D-idose and D-glucose.

In FIG. 1, it is shown that the L-sugars are generally produced from the basic material, D-glucose. According to the present process, an aqueous solution of D-glucose is hydrogenated, preferably in a fixed catalyst bed. This hydrogenation provides an aqueous solution of D-sorbitol. A certain amount of D-mannitol (i.e., less than 10%) is also formed. This can be removed by cooling, upon which it crystallizes preferentially over D-sorbitol, and filtering.

The aqueous D-sorbitol solution is then treated with oxygen or air in the presence of specific oxidizing microbes, i.e., *Gluconobacter suboxydans*, which are also referred to as *Acetobacter suboxydans*. The D-sorbitol after being oxygenated, provides L-sorbose which is treated, i.e., raceimized, by addition of an alkaline substance (i.e., hydroxy ion) such as sodium hydroxide and converted to a mixture of L-sorbose, L-idose and L-gulose. In this conversion, there is an equilibrium which is established where all three isomers are present. This racemization reaction proceeds readily at temperatures of from 20° to 80° C.; temperatures ranging from about 25 to about 60° C. being preferable. The reaction time at 25° to 35° C. varies from 56 to 14 hours, but at higher temperatures, the racemization proceeds faster. The unconverted L-sorbose is recycled.

The remaining unracemized L-sorbose is precipitated from the mixture in the separation step with lime from a dilute solution, i.e., a 6 to 7% aqueous solution and then cooled. This precipitation utilizes the principles of "Steffan's Process" in which sucrose is separated by means of a lime salt known as calcium saccharate. In the present process, the L-sugars mixture is diluted to 6 to 7 percent and cooled to below about 20° C. Finely pulverized lime is added with agitation to form a precipitate of calcium L-sorbate. This precipitate (containing about 90 percent of L-sorbose) is filtered. The filtrate is heated, during which another precipitation occurs and this too is filtered. Cold precipitate is removed by vacuum filtration, and hot precipitate, by a thickener. Both precipitates are mixed with water and carbonated, where the lime precipitates are decomposed into $CaCO_3$ and L-sorbose which is recycled.

The solution of L-idose and L-gulose from which the L-sorbose was precipitated, is passed from its separator to a fractional crystallizer. From the crystallizer, crystalline L-sugars, i.e., L-idose and L-gulose, are provided. Also, from the crystallizer, additional L-sorbose is recovered and recycled.

The present process in producing L-sugars from D-glucose uses 5 to 60% aqueous glucose feed solutions, and preferably 10 to 40% aqueous glucose solutions. Also, according to the present invnetion, in place of the pure D-glucose, a solution of crude starch hydrolyzate can be used for producing the D-sorbitol and eventually the L-sugars, i.e., L-idose and L-gulose, which can be crystallized from their aqueous solution.

Also, in the present solution, the intermediate product D-sorbitol should be noted since D-sorbitol is quite costly to manufacture. However, it has been found, according to the process disclosed in U.S. Ser. No. 258,225, that sorbitol can be economically produced. Accordingly, the present disclosure includes by reference the process disclosed in U.S. Ser. No. 258,225; filed Apr. 27, 1981.

In the hydrogenation of D-glucose with the fixed catalyst bed, the hydrogen flow rate is related to the liquid feed rate and to the quantity of catalyst used, as the hydrogen gas flow provides for carrying the feed liquid droplets through the fixed-catalyst type beds to achieve intimate contact with the catalyst practicles. The liquid feed rate in the present hydrogenation ranges from about 0.3 to about 10.0 g./hr./g. of catalyst, and preferably from about 0.4 to about 8.0 g./hr/g. of catalyst. Accordingly, the ratio of hydrogen gas to liquid feed rate at standard conditions range from about 500 to about 5000 for achieving satisfactory conversion of D-glucose to D-sorbitol.

The catalyst used in the fixed bed may be any suitable catalyst for the conversion or treatment of D-glucose to provide D-sorbitol. The catalyst found to be most preferable is a reduced and stabilized nickel on an inert support such as silica-alumina. The catalyst contains at least about 40 W % nickel and up to about 70 W % nickel.

The aerobic fermenting bacteria, include: *Gluconobacter suboxydans* (subsp. suboxydans). The amount of *suboxydans* used in a continuous process with cell recycle is generally related to the amount of D-sorbitol fed. This amount ranges from about 20 g. to about 80 g./hr./g. of catalyst.

In the conversion of the L-sorbose in an alkaline solution, this solution may be a 1.0 N solution of a hydroxide such as sodium hydroxide or calcium hydroxide.

The conditions under which the D-glucose is hydrogenated to D-sorbitol in the fixed catalyst bed is at a temperature ranging from about 100° to about 150° C. and a pressure ranging from about 500 to about 2000 psig hydrogen partial pressure.

The conversion of L-sorbose to the L-sugars takes place generally at a temperature ranging from about 20° to about 80° C.

According to the present invention, the L-sugars, i.e., L-idose and L-gulose, may be produced from other starting materials than D-glucose. The L-sugars can be prepared from commercially available D-sorbitol or L-sorbose. For example, the L-sugars (i.e., L-idose and L-gulose) can be produced from D-sorbitol by oxidizing the D-sorbitol to provide L-sorbose, racemizing the L-sorbose to provide a mixture of L-sorbose, L-idose and L-gulose, and precipitating the remaining L-sorbose with lime from a dilute solution.

The L-sugars, i.e., L-idose and L-gulose, may be utilized as a sweetening material for foodstuffs of all kinds. The L-sugars are a sweetening agent which are non-calorific and less susceptible to spoilage due to the growth of various micro-organisms than those prepared with conventional saccharide sweetening agents. For example, one real problem associated with the use of formation such as syrups that are prepared from conventional saccharide sweeteners such as in the soft drinks is the decomposition due to bacterial growth. Since the L-hexoses (i.e., L-sugars) sweetening agents of the present invention provide little or no nutrient value for the various micro-organisms, their growth and, hence, the corresponding spoilage of these formations is drastically reduced.

I claim:

1. A method of producing L-sugars including L-idose and L-gulose from D-glucose, which comprises the steps of:
    (a) hydrogenating D-glucose to provide D-sorbitol;
    (b) oxidizing said D-sorbitol to provide L-sorbose;
    (c) racemizing said L-sorbose to provide a mixture of L-sorbose, L-idose and L-gulose; and
    (d) precipitating the unracemized L-sorbose under cooling with lime from a dilute solution.

2. The method according to claim 1, wherein the unracemized L-sorbose is recycled.

3. The method according to claim 1, wherein said hydrogenation of D-glucose the ratio of hydrogen gas to liquid feed rate of said D-glucose ranges from about 500 to 5000.

4. The method according to claim 1, wherein said D-glucose is in a 5 to 60% aqueous solution.

5. The method according to claim 1, wherein said D-glucose is in a 10 to 40% aqueous solution.

6. The method according to claim 1, wherein said D-glucose is hydrogenated in a fixed catalyst bed at a temperature ranging from about 100° to about 150° C.

7. The method according to claim 1, wherein said L-sorbose is racemized at a temperature ranging from about 20° to 80° C.

8. The method according to claim 1, wherein said L-sorbose is racemized to a mixture of L-sorbose, L-idose and L-gulose in a 1.0N alkaline solution.

9. The method according to claim 1, wherein said L-sorbose is precipitating with lime from a 6 to 7% aqueous solution.

10. The method according to claim 1, wherein L-idose and L-gulose are recovered by crystallization from a solution after removal of calcium L-sorbate.

11. The method according to claim 1, wherein the oxidation of D-sorbitol to L-sorbose is carried out with an oxygen containing gas in the presence of *Gluconobacter suboxydans*.

12. A method of producing L-sugars including L-idose and L-gulose from D-sorbitol which comprises the steps of:
    (a) oxidizing D-sorbitol to provide L-sorbose;
    (b) racemizing said L-sorbose to provide a mixture of L-sorbose, L-idose and L-gulose; and
    (c) precipitating the unracemized L-sorbose under cooling with lime from a dilute solution.

13. The method according to claim 12, wherein the unracemized L-sorbose is recycled.

14. The method according to claim 12, wherein said L-sorbose is racemized to a mixture of L-sorbose, L-idose and L-gulose in a 1.0N alkaline solution.

15. The method according to claim 12, wherein said L-sorbose is precipitated with lime from a 6 to 7% aqueous solution.

16. The method according to claim 13, wherein L-idose and L-gulose are recovered by crystallization from a solution after removal of calcium L-sorbate.

17. The method according to claim 12, wherein said L-sorbose is racemized at a temperature ranging from about 20° to about 80° C.

18. A method of producing L-sugars including L-idose and L-gulose from L-sorbose which comprises the steps of:
    (a) racemizing L-sorbose to provide a mixture of L-sorbose L-idose and L-gulose; and
    (b) precipitating the unracemized L-sorbose under cooling with lime from a dilute solution.

19. The method according to claim 18, wherein the unracemized L-sorbose is recycled.

20. The method according to claim 18, wherein said L-sorbose is racemized to a mixture of L-sorbose, L-idose and L-gulose, in a 1.0 N alkaline solution.

21. The method according to claim 18, wherein said L-sorbose is precipitated with lime from a 6 to 7% aqueous solution.

22. The method according to claim 18, wherein L-idose and L-gulose are recovered by crystallization from a solution after removal of clacium L-sorbate.

23. The method according to claim 18, wherein said L-sorbose is racemixed at a temperature ranging from about 20° to about 80° C.

* * * * *